US011972540B2

(12) United States Patent
Tanaka et al.

(10) Patent No.: US 11,972,540 B2
(45) Date of Patent: Apr. 30, 2024

(54) IMAGE PROCESSING APPARATUS, MEDICAL IMAGING APPARATUS, AND IMAGE PROCESSING PROGRAM

(71) Applicant: Hitachi, Ltd., Tokyo (JP)

(72) Inventors: Chizue Tanaka, Tokyo (JP); Yukio Kaneko, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 433 days.

(21) Appl. No.: 17/214,970

(22) Filed: Mar. 29, 2021

(65) Prior Publication Data

US 2021/0407048 A1    Dec. 30, 2021

(30) Foreign Application Priority Data

Jun. 25, 2020    (JP) ................. 2020-109420

(51) Int. Cl.
*G06T 5/00*    (2006.01)
*G06T 7/00*    (2017.01)
*G16H 30/20*    (2018.01)
*G16H 30/40*    (2018.01)

(52) U.S. Cl.
CPC ............ *G06T 5/002* (2013.01); *G06T 7/0012* (2013.01); *G16H 30/20* (2018.01); *G16H 30/40* (2018.01)

(58) Field of Classification Search
CPC ......... G06T 5/002; G06T 5/50; G06T 7/0012; G06T 2207/10088; G06T 2207/20081; G06T 2207/20084; G06T 2207/20221; G16H 30/20; G16H 30/40; G06F 3/0482;

(Continued)

(56) References Cited

U.S. PATENT DOCUMENTS

| 11,348,226 B2* | 5/2022 | Ida .................. A61B 5/055 |
| 2008/0310695 A1 | 12/2008 | Garnier et al. |
| 2017/0061620 A1* | 3/2017 | Park .................. G06T 5/50 |

(Continued)

FOREIGN PATENT DOCUMENTS

| JP | 2007-503903 A | 3/2007 |
| JP | 2014-210175 W | 11/2014 |

(Continued)

OTHER PUBLICATIONS

Japanese Office Action received in corresponding Japanese Application No. 2020-109420 dated Dec. 5, 2023.

*Primary Examiner* — Nay A Maung
*Assistant Examiner* — Jose M Torres
(74) *Attorney, Agent, or Firm* — MATTINGLY & MALUR, PC (57) ABSTRACT

Provided are an image processing apparatus, a medical imaging apparatus, and an image processing program that remove noise from an image having different noise levels depending on regions in the image at a low calculation cost, and enable high quality according to a preference of a reader. A plurality of image generators receive measurement data or a captured image obtained by an image data acquisition apparatus and generate different images for a same imaging range. An image selection and combination unit selects different image regions from a plurality of images generated by the plurality of image generators according to a predetermined region selection pattern, and generates one image by combining the images of the selected image regions.

19 Claims, 9 Drawing Sheets

(58) Field of Classification Search
CPC ............. G06F 3/04845; G06F 3/04847; G06F 3/04855
See application file for complete search history.

(56) References Cited

U.S. PATENT DOCUMENTS

| | | | |
|---|---|---|---|
| 2019/0004132 A1* | 1/2019 | Tan | G01R 33/4818 |
| 2019/0195975 A1* | 6/2019 | Liu | G01R 33/561 |
| 2020/0294229 A1* | 9/2020 | Schlemper | G01R 33/445 |
| 2020/0341094 A1* | 10/2020 | Polak | A61B 5/7207 |

FOREIGN PATENT DOCUMENTS

| | | | |
|---|---|---|---|
| JP | 2018-108365 A | 7/2018 | |
| JP | 2018-198682 W | 12/2018 | |
| JP | 2019-25044 W | 2/2019 | |
| JP | 2019-111322 A | 7/2019 | |
| JP | 2019-180637 W | 10/2019 | |
| JP | 2019-208990 A | 12/2019 | |
| JP | 2020-92739 W | 6/2020 | |
| WO | 2005/058165 A1 | 6/2005 | |
| WO | 2015/045144 A1 | 4/2015 | |

\* cited by examiner

(12) United States Patent — US 11,972,540 B2

IMAGE PROCESSING APPARATUS, MEDICAL IMAGING APPARATUS, AND IMAGE PROCESSING PROGRAM

CROSS-REFERENCE TO RELATED APPLICATION

The present application claims priority from Japanese application JP2020-109420, filed on Jun. 25, 2020, the contents of which is hereby incorporated by reference into this application.

BACKGROUND OF THE INVENTION

1. Field of the Invention

The present invention relates to an apparatus that generates a medical image with reduced noise.

2. Description of the Related Art

In a medical imaging apparatus such as a magnetic resonance imaging (hereinafter, referred to as MRI) apparatus, an X-ray computed tomography (CT) apparatus, and an ultrasonic diagnostic apparatus, if it takes a long time for capturing in order to acquire data (or a signal) for reconstructing an image, an adverse effect such as a burden on a subject or appearance of an image artifact due to movement of the subject is exerted. Therefore, a high-speed capturing method for shortening a capturing time by devising a capturing method is developed in each modality.

For example, in an MRI apparatus, a high-speed capturing method (for example, parallel imaging) in which the capturing time is shortened by undersampling a k-space using a plurality of reception coils and an image is reconstructed by calculation using a sensitivity distribution of the reception coils is put into practical use. However, in the high-speed capturing method of the MRI apparatus, since an amount of data used for the image is smaller than usual in order to increase the speed, noise is generated and image quality is deteriorated. In addition, a noise distribution in the same capturing plane is not uniform with respect to a capturing space.

Further, in an ultrasonic capturing apparatus, noise is particularly increased in a deep region or the like where sensitivity is insufficient.

Several image quality improvement techniques are developed as methods for solving such deterioration in the image quality. For example, JP-T-2007-503903 (Patent Literature 1) discloses a technique of reducing noise of an entire image for reconstructed images including noise having spatial fluctuation (non-uniformity) as in the parallel imaging of the MRI apparatus. Specifically, a noise map representing variance of the noise contained in the reconstructed images is generated, a locally adaptive nonlinear noise filter is generated based on the noise map, and the reconstructed images are sequentially processed by the generated filter, thereby reducing non-uniform noise from the entire image.

In the image quality improvement technique of Patent Literature 1, it is necessary to generate the noise map for each image that changes depending on an imaging condition, a state of a subject, or the like, generate the nonlinear noise filter based on the noise map, and sequentially apply the nonlinear noise filter to the images. For this reason, a calculation cost for filter generation increases. In addition, since the generated nonlinear noise filter is sequentially applied to the images, the calculation cost also increases at the time of filter processing. Further, since the image viewed by a reader is an image after the image quality is improved by the generated filter, there is a problem that a preference of the reader cannot be reflected in adjustment of the filter itself.

SUMMARY OF THE INVENTION

An object of the invention is to remove noise from an image having different noise levels depending on regions in the image at a low calculation cost, and to enable high quality according to a preference of a reader.

According to an aspect of the invention, there is provided an image processing apparatus including: a plurality of image generators configured to receive measurement data or a captured image obtained by a capturing apparatus and generate different images for a same imaging range; and an image selection and combination unit configured to select different image regions from the plurality of images generated by the plurality of image generators according to a predetermined region selection pattern, and generate one image by combining the images of the selected image regions.

According to the invention, it is possible to remove noise from an image having different noise levels depending on regions in the image at a low calculation cost. In addition, it is possible to achieve high quality according to a preference of a reader.

DESCRIPTION OF THE PREFERRED EMBODIMENTS

A medical image capturing apparatus according to an embodiment of the invention will be described.

First Embodiment

A medical imaging apparatus according to a first embodiment includes an MRI apparatus as an image data acquisition apparatus. The medical imaging apparatus according to the first embodiment will be described with reference to FIGS. 1 to 6.

Figure 1:
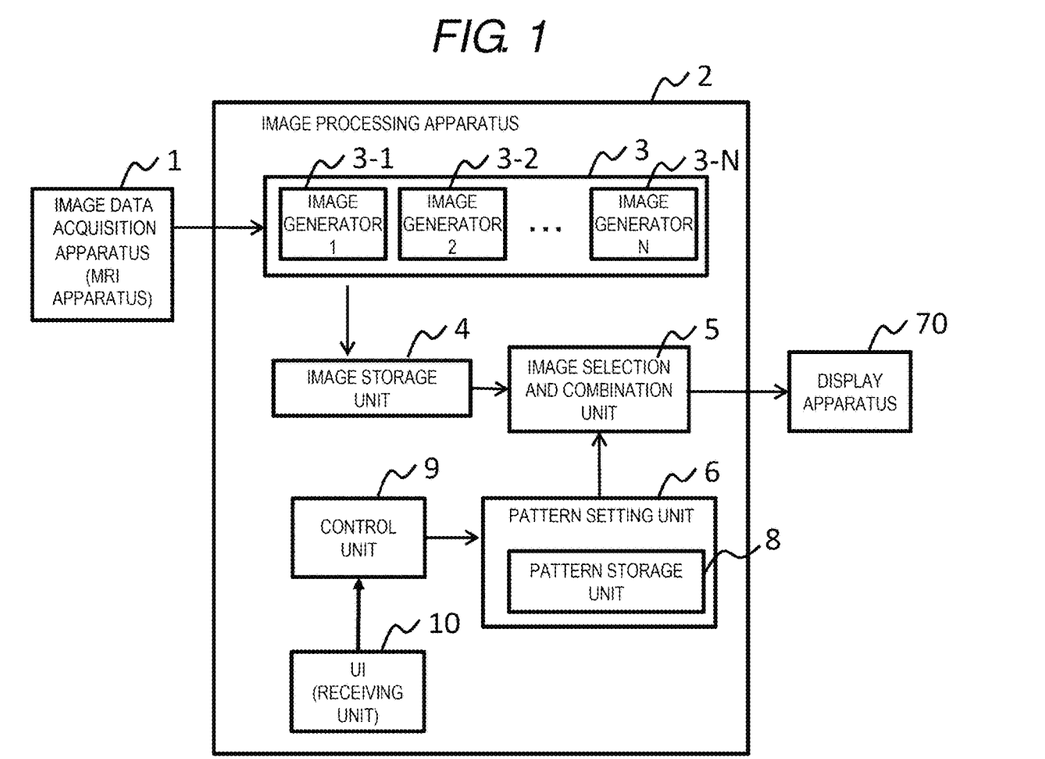
FIG. 1 is a block diagram showing a configuration of a medical imaging apparatus according to a first embodiment.
Figure 2:
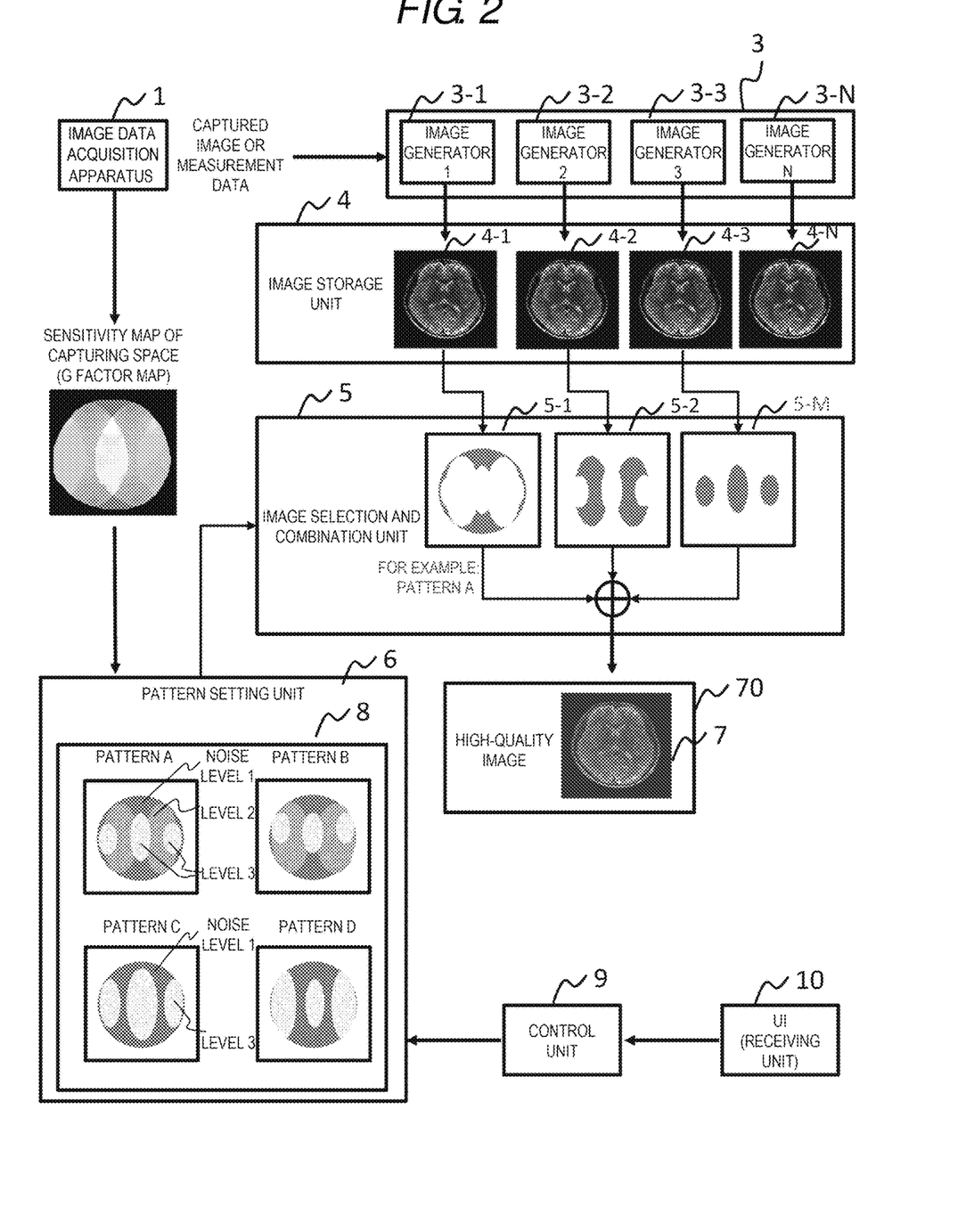
FIG. 2 is a block diagram showing the configuration of the medical imaging apparatus according to the first embodiment and a flow of processing.

As shown in FIGS. 1 and 2, the medical imaging apparatus according to the first embodiment includes an image data acquisition apparatus 1 and an image processing apparatus 2. The image data acquisition apparatus 1 is the MRI apparatus.

<Configuration of Image Processing Apparatus 2>

The image processing apparatus 2 includes a plurality of image generators 3-1 to 3-N, an image selection and combination unit 5, an image storage unit 4, a pattern setting unit 6, a receiving unit 10, and a control unit 9.

The image generators 3-1 to 3-N receive measurement data or a captured image (referred to as an original image) obtained by the image data acquisition apparatus 1, and generate different images 4-1 to 4-N for a same imaging range as the original image. Specifically, the image generators 3-1 to 3-N are configured in advance to generate high-quality images 4-1 to 4-N from images of a predetermined noise level, respectively.

For example, the original image obtained by the image data acquisition apparatus 1 is an image captured and reconstructed by parallel imaging in a high-speed capturing method. When the noise level of a spatial region of the image differs in, for example, three stages, the image generators 3-1 to 3-3 generate highest quality images 4-1 to 4-3 with reduced noise in each of the predetermined noise level regions. Specifically, for example, when the image generator 3-1 is configured to correspond to a noise level 1, which is a lowest noise level, the image generator 3-1 generates the high-quality image 4-1, which is an image in the same imaging range as the original image, and in which the noise in a region corresponding to the region of the noise level 1 in the original image is most reduced. At this time, in the high-quality image 4-1, the image quality in regions corresponding to regions of noise levels 2 and 3 in the original image is not as high as that in the region corresponding to the region of the noise level 1.

Similarly, when the image generator 3-2 is configured to correspond to the noise level 2, the image generator 3-2 generates the high-quality image 4-2, which is an image in the same imaging range as the original image, and in which the noise in a region corresponding to a region of the noise level 2 in the original image is most reduced. Further, when the image generator 3-3 is configured to correspond to the noise level 3 having the highest noise level, the image generator 3-3 generates the high-quality image 4-3, which is an image in the same imaging range as the original image, and in which the noise in a region corresponding to the region of the noise level 3 in the original image is most reduced.

In reconstruction processing of the parallel imaging, the noise level in the spatial region of the image can be calculated based on distribution information of a G factor (G factor map) representing an index of an amount of noise to be propagated. For example, any range of values of the G factor, such as the value of the G factor of 1.1 or less for the noise level 1, 1.1 to 1.2 for the noise level 2, and 1.2 to 2.0 for the noise level 3, can be used for noise level division.

Figure 3:
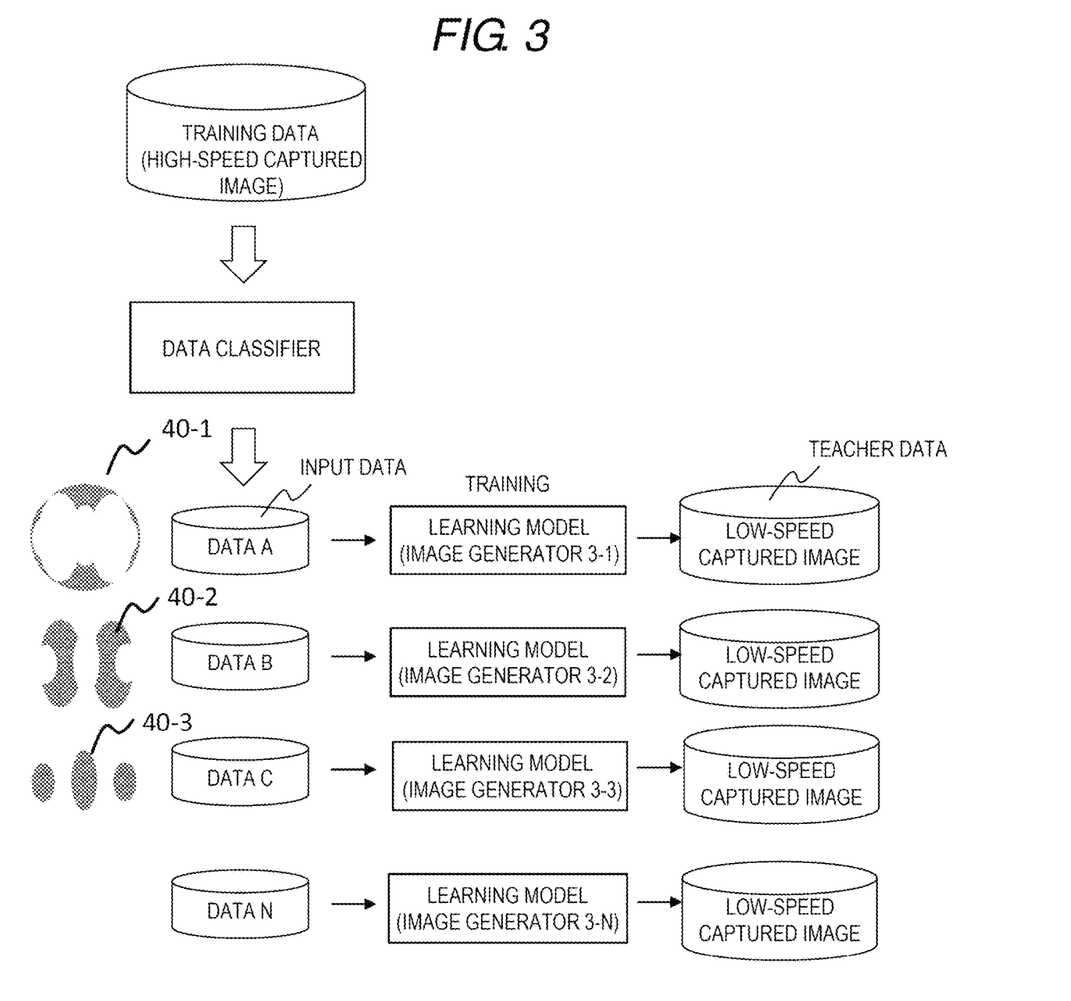
FIG. 3 is an illustrative diagram showing training data of an image generator (learning model) of the medical imaging apparatus according to the first embodiment.

Each of the image generators 3-1 to 3-N can be implemented by a trained learning model (for example, a neural network). Specifically, as shown in FIG. 3, the captured image obtained by high-speed capturing such as the parallel imaging by the image data acquisition apparatus 1 is divided into small areas of a predetermined size by a data classifier, the noise level of the small areas is calculated based on the G factor map as described above, the small areas is extracted for each of the noise levels 1 to N, and classified images 40-1 to 40-N are generated. The images 40-1 to 40-N are sets of small areas images of the noise levels 1 to N, respectively. The images 40-1 to 40-N are input data to the learning models (image generators 3-1 to 3-N), respectively.

For example, the image 40-1 of a set of small areas of the noise level 1 is used as an input of the learning model of the image generator 3-1. Similarly, the image 40-2 of a set of small areas of the noise level 2 is used as an input of the learning model of the image generator 3-2. The image 40-3 of a set of small areas of the noise level 3 is used as an input of the learning model of the image generator 3-3.

On the other hand, as teacher data (correct data) of each learning model, an image obtained by a low-speed capturing method (for example, full sampling capturing method) in which the high-quality image can be obtained by the image data acquisition apparatus 1 is used.

The learning model is trained using the input data and the teacher data, and weighting of nodes in the neural network is set in advance. Accordingly, the image generators 3-1 to 3-N can be made.

The image generators 3-1 to 3-N can generate the images 4-1 to 4-N having different regions with the highest quality by inputting the same captured image.

The image storage unit 4 stores the images 4-1 to 4-N generated by the respective image generators 3-1 to 3-N.

The image selection and combination unit 5 selects different image regions 5-1 to 5-M (here, M=3) from the images 4-1 to 4-N according to a region selection pattern set by the pattern setting unit 6, and combines the images of the selected image regions 5-1 to 5-M to generate one high-quality image 7. The image regions 5-1 to 5-M selected by the image selection and combination unit 5 are regions in which the generated images 4-1 to 4-N of the image generators 3-1 to 3-3 have the highest quality. Therefore, the image selection and combination unit 5 can generate the high-quality image 7 for the whole image by selecting and combining the regions having the highest quality from the generated images 4-1 to 4-N, respectively. The image selection and combination unit 5 displays the generated high-quality image 7 on a display apparatus 70.

As described above, according to the first embodiment, it is possible to remove the noise from an MRI image including the noise with different levels depending on the regions at a low calculation cost.

A number M of the regions selected by the image selection and combination unit 5 is the number of stages of the noise levels set in the region selection pattern, and is equal to or less than N. The number M of regions to be selected may be set to a different number depending on the region selection pattern.

The pattern setting unit 6 includes a pattern storage unit 8 in which a plurality of types of region selection patterns are stored in advance. The pattern setting unit 6 may be configured to receive the G factor map of the captured image (original image) from the image data acquisition apparatus 1, select the region selection pattern corresponding to the G factor map from the pattern storage unit 8, and set the region selection pattern in the image selection and combination unit 5.

The receiving unit 10 may receive a selection instruction of the region selection pattern from a user. In this case, the pattern setting unit 6 receives the selection instruction via the control unit 9, and selects the instructed region selection pattern. Accordingly, it is possible to generate the high-quality image 7 according to the preference of the user.

When, after the image selection and combination unit 5 generates one high-quality image 7 according to the set region selection pattern, the receiving unit 10 receives the selection of the region selection pattern from the user, and the pattern setting unit 6 sets the region selection pattern in the image selection and combination unit 5, the image selection and combination unit 5 generates an image according to the set region selection pattern using the images 4-1 to 4-N stored in the image storage unit 4. Accordingly, the high-quality images 7 can be repeatedly generated according to different region selection patterns without the image generators 3-1 to 3-N regenerating the images 4-1 to 4-N from the captured image.

The image selection and combination unit 5 generates a binary map of each region selection pattern and multiplies the image received from the image storage unit 4 to generate the image regions 5-1 to 5-3. By overlapping the image regions at the same coordinates (performing addition processing), it is possible to generate an image from which the noise of the entire original image is removed. At this time, unnatural discontinuity may occur in the image due to a difference in noise removal performance at boundaries of the image regions 5-1 to 5-3. In order to avoid this, the region selection pattern is set in advance so that the boundaries overlap with one another by a predetermined width. In order to smooth the boundaries at the time of combination, the image selection and combination unit 5 weights the images in the image regions 5-1 to 5-3 in the overlapping regions, and adds those weighted image regions 5-1 to 5-3 each other. A weighting function applied in the overlapping regions is preferably a function in which the capturing region of a subject is all 1, and a raised cosine function or the like can be used.

Figure 4:
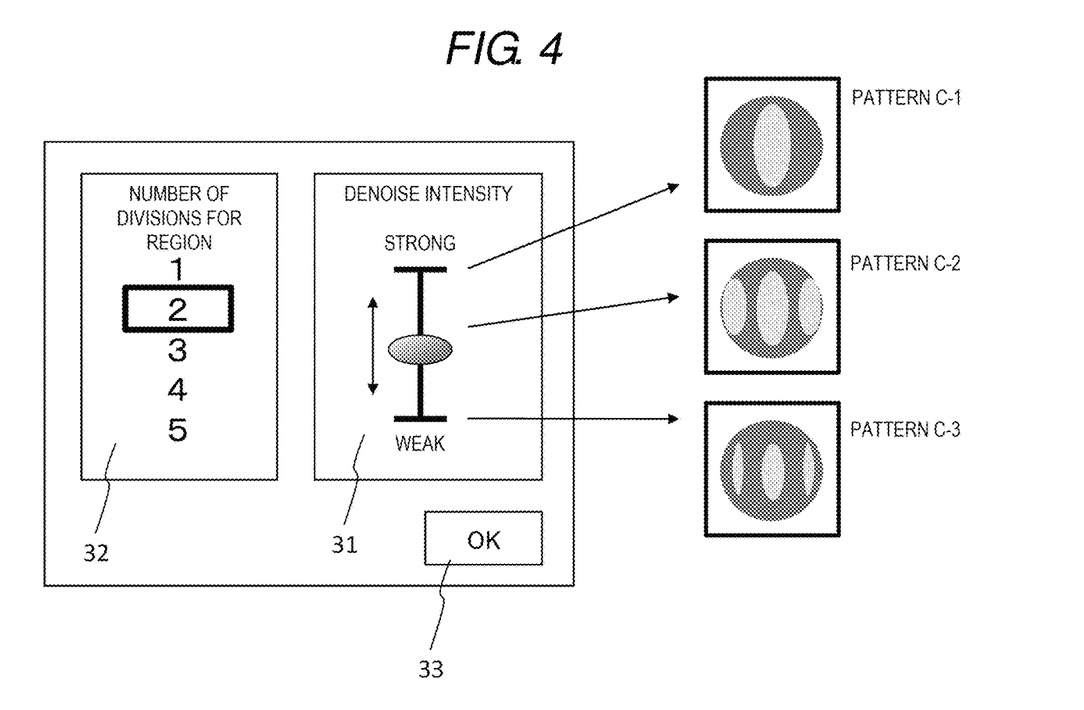
FIG. 4 is an illustrative diagram showing a slide bar as an example of a receiving unit according to the first embodiment.

In addition, the receiving unit 10 may be a slide bar 31 in which region selection patterns C-1, C-2, and C-3 are associated with respective slide positions in advance as shown in FIG. 4. In accordance with the position of the slide bar 31 slid by the user, the pattern setting unit 6 sets the region selection pattern associated with the position in the image selection and combination unit 5. Accordingly, the user can display a desired high-quality image 7 by looking at the image 7 displayed on the display apparatus 70 while sliding the slide bar 31 and stopping the slide bar 31 at a desired position and selecting the OK button 33.

As shown in FIG. 4, the region selection pattern associated with each position of the slide bar 31 may be set so that the number of stages of the noise level (number of divisions: for example, two stages of the noise levels 1 and 2) does not change depending on the slide position but only a shape of the region changes. In this case, as shown in FIG. 4, by providing an operation unit 32 for the user to select the number of stages of the noise level (number of divisions), a plurality of types of region selection patterns can be selected by one slide bar 31.

However, the present embodiment is not limited to a form in which the number of stages of the noise level (number of divisions) does not change depending on the slide position, and patterns having different numbers of divisions may be associated depending on the slide position.

A user interface for selecting the region selection pattern is not limited to the form of the slide bar. For the user interface, any operation receiving unit capable of setting a degree of change by the operation of the user, such as a form of a physical slide bar, a rotary knob, or a touch panel for selecting and inputting a numerical value may be used, and may take various forms.

<Operation of Image Processing Apparatus 2>

Figure 5:
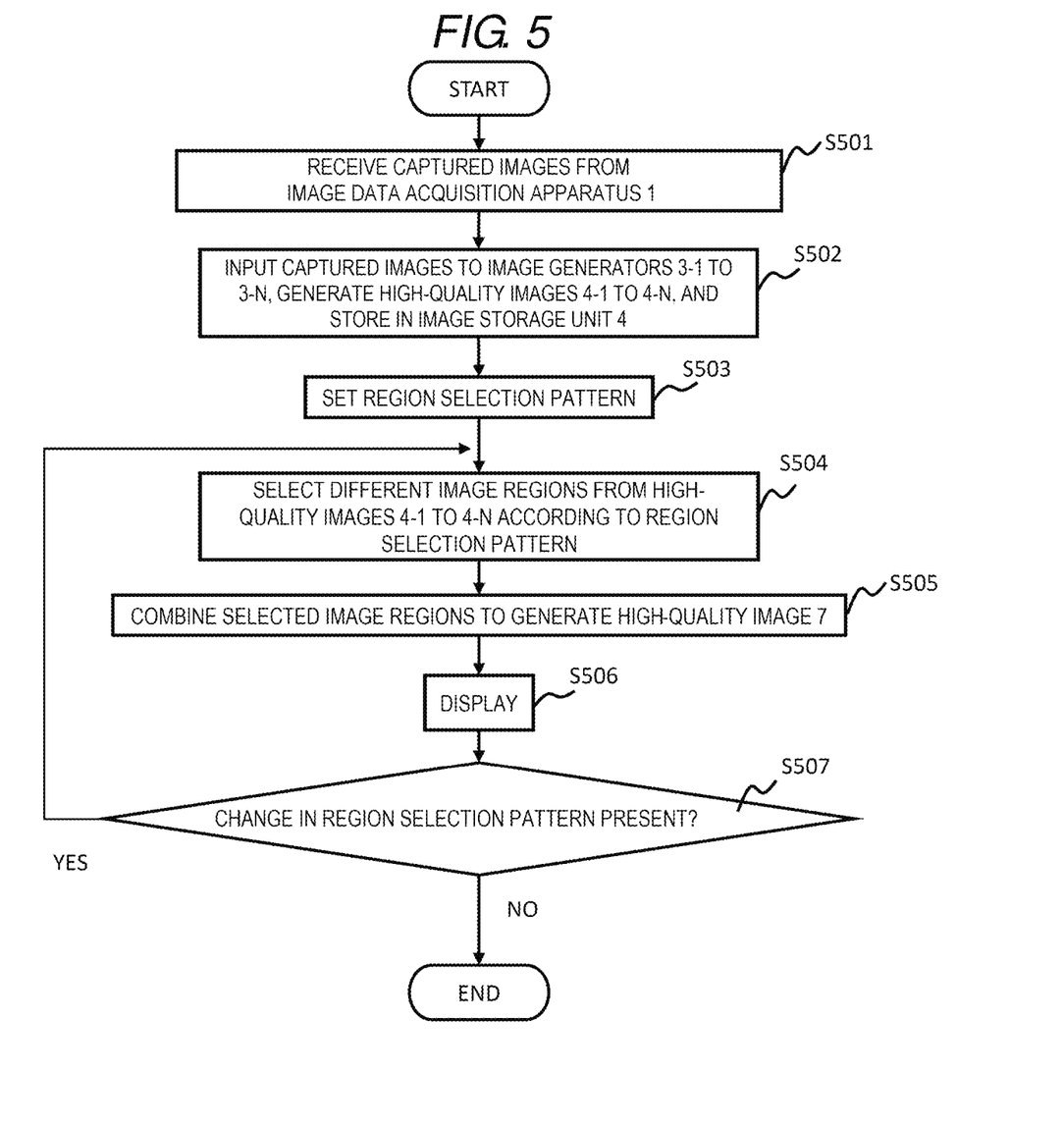
FIG. 5 is a flowchart showing an operation of an image processing apparatus of the medical imaging apparatus according to the first embodiment.

Next, the operation of the image processing apparatus 2 will be described with reference to a flowchart in FIG. 5.

The image processing apparatus 2 is constituted by a computer or the like including a processor such as a central processing unit (CPU) or a graphics processing unit (GPU), and a memory. The CPU reads and executes a program stored in the memory, thereby implementing functions of the image generators 3-1 to 3-N, the image selection and combination unit 5, and the pattern setting unit 6 by software. A part or all of the image generators 3-1 to 3-N, the image selection and combination unit 5, and the pattern setting unit 6 may be implemented by hardware. For example, a circuit design may be performed so as to implement the functions of the image generators 3-1 to 3-N, the image selection and combination unit 5, and the pattern setting unit 6 using a custom IC such as an application specific integrated circuit (ASIC) or a programmable IC such as a field-programmable gate array (FPGA).

The image generator 3 receives the captured images from the image data acquisition apparatus 1 (step S501). The image generator 3 inputs the received captured images to the image generators 3-1 to 3-N. The image generators 3-1 to 3-N generate the high-quality images 4-1 to 4-N according to the corresponding noise levels, and store the high-quality images 4-1 to 4-N in the image storage unit 4 (step S502).

The pattern setting unit 6 receives the G factor map from the image data acquisition apparatus 1, selects the region selection pattern corresponding to the G factor map, and sets the selected region selection pattern in the image selection and combination unit 5 (step S503).

The image selection and combination unit 5 selects (extracts) the region of each noise level of the set region selection pattern from the high-quality images 4-1 to 4-N corresponding to the noise levels. Accordingly, different regions are selected from the high-quality images 4-1 to 4-N (step S504).

The image selection and combination unit 5 combines the regions selected in step S504 to generate one high-quality image 7 (step S505).

The image selection and combination unit 5 displays the high-quality image generated in step S505 on the display apparatus 70 (step S506).

When the receiving unit 10 receives the setting (change) of the region selection pattern from the user, the processing returns to step S504 and the pattern setting unit 6 selects a region in accordance with the set (changed) region selection pattern (step S507).

As described above, according to the present embodiment, it is possible to remove the noise from the image including the noise with different levels depending on the regions at the low calculation cost. Moreover, the region selection pattern can be changed in accordance with the preference of the user (reader) to repeatedly generate the high-quality image.

<Overall Configuration of MRI Apparatus>

Next, an overall structure of the capturing apparatus (MRI apparatus) 1 according to the present embodiment will be described with reference to FIG. 6.

Figure 6:
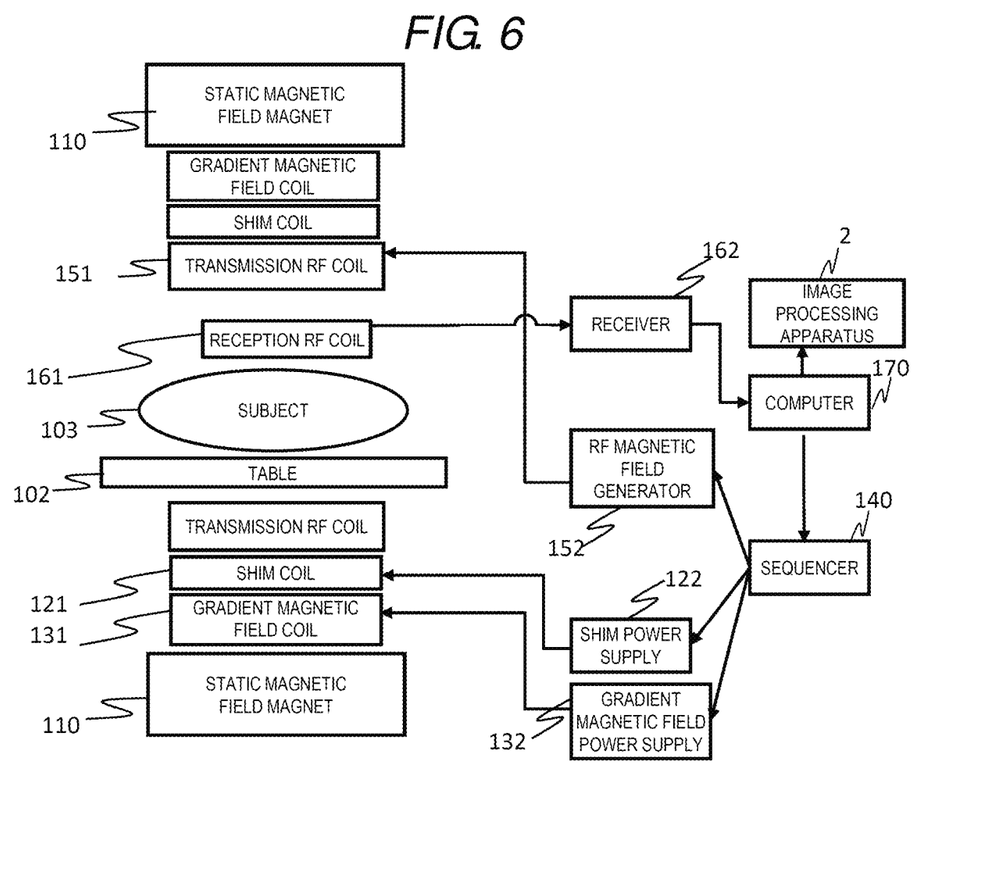
FIG. 6 is a block diagram showing a configuration of an MRI apparatus as a capturing apparatus of the medical imaging apparatus according to the first embodiment.

As shown in FIG. 6, the MRI apparatus 1 includes a static magnetic field magnet (static magnetic field generation unit) 110, a gradient magnetic field coil (gradient magnetic field generation unit) 131, a transmission RF coil 151, a reception RF coil 161, a gradient magnetic field power supply 132, a shim coil 121, a shim power supply 122, an RF magnetic field generator 152, a receiver 162, a magnetic coupling prevention circuit drive device 180, a computer (image reconstruction unit) 170, and a sequencer 140. A reference numeral 102 denotes a table on which a capturing portion of a subject 103 is placed in the capturing space.

The static magnetic field magnet 110 generates a static magnetic field in the capturing space. The static magnetic field magnet 110 may be a tunnel magnet that generates the static magnetic field in a horizontal direction by a solenoid coil, or may use a static magnetic field magnet that generates the static magnetic field in a vertical direction.

The gradient magnetic field coil 131 is connected to the gradient magnetic field power supply 132 and generates a gradient magnetic field in the capturing space. The shim coil 121 is connected to the shim power supply 122 and adjusts uniformity of the static magnetic field.

The transmission RF coil 151 is connected to the RF magnetic field generator 152, and irradiates (transmits) the subject 103 with an RF magnetic field. A frequency of the RF magnetic field is set to a frequency that excites nuclear magnetism of atomic nuclei (protons or the like) of a nuclide of the subject 103 desired to be captured. As the transmission RF coil 151, any structure may be used. For example, a birdcage type RF coil can be used.

The reception RF coil 161 is connected to the receiver 162, and receives a nuclear magnetic resonance signal from the subject 103. Here, a multi-channel RF coil (array coil) including a plurality of coil units is used as the reception RF coil 161 according to the present embodiment. Accordingly, the high-speed capturing can be performed by the parallel imaging method.

The sequencer 140 sends a command to the gradient magnetic field power supply 132 and the RF magnetic field generator 152 to operate the gradient magnetic field power supply 132 and the RF magnetic field generator 152. The command is sent in accordance with an instruction from the computer 170. In addition, the sequencer 140 sets a magnetic resonance frequency as a reference for detection in the receiver 162 in accordance with the instruction from the computer 170. Specifically, at the time of capturing, the subject 103 is irradiated with the gradient magnetic field and the RF magnetic field from the gradient magnetic field coil 131 and the transmission RF coil 151 at predetermined timings, respectively, in accordance with the command from the sequencer 140. The nuclear magnetic resonance signal generated by the subject 103 is received by the reception RF coil 161 and detected by the receiver 162. Accordingly, a capturing pulse sequence for implementing the predetermined capturing method is executed.

The computer 170 controls the overall operation of the MRI apparatus 1 and performs various kinds of signal processing. For example, a signal detected by the receiver 162 is received via an A/D conversion circuit (not shown), and signal processing such as image reconstruction is performed.

The detected signal and the measurement condition are stored in a storage medium as necessary. In addition, the computer 170 sends a command to the sequencer 140 so that each device operates at a timing and intensity programmed in advance. Further, when it is necessary to adjust the uniformity of the static magnetic field, the computer 170 sends a command to the shim power supply 122 via the sequencer 140, and causes the shim coil 121 to adjust the uniformity of the static magnetic field.

When performing the parallel imaging, phase encoding is thinned out every other line to shorten an execution time of the capturing pulse sequence and to achieve the high-speed capturing. At the time of image reconstruction, the image reconstruction is performed using a sensitivity map of the array coil.

Second Embodiment

As a medical imaging apparatus according to a second embodiment, an ultrasonic imaging apparatus is provided as the image data acquisition apparatus 1. The medical imaging apparatus according to the second embodiment will be described with reference to FIGS. 7 to 9.

<Configuration of Image Processing Apparatus 2>

Figure 7:
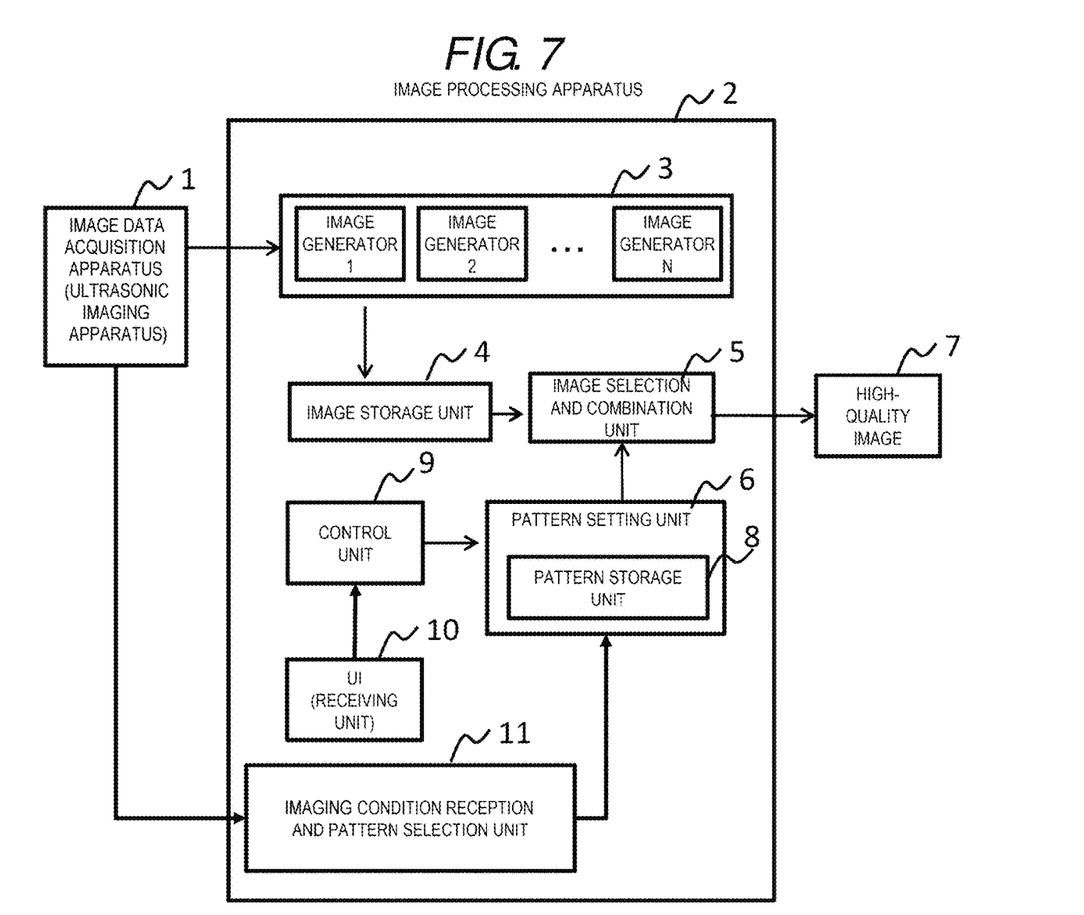
FIG. 7 is a block diagram showing a configuration of a medical imaging apparatus according to a second embodiment.
Figure 8:
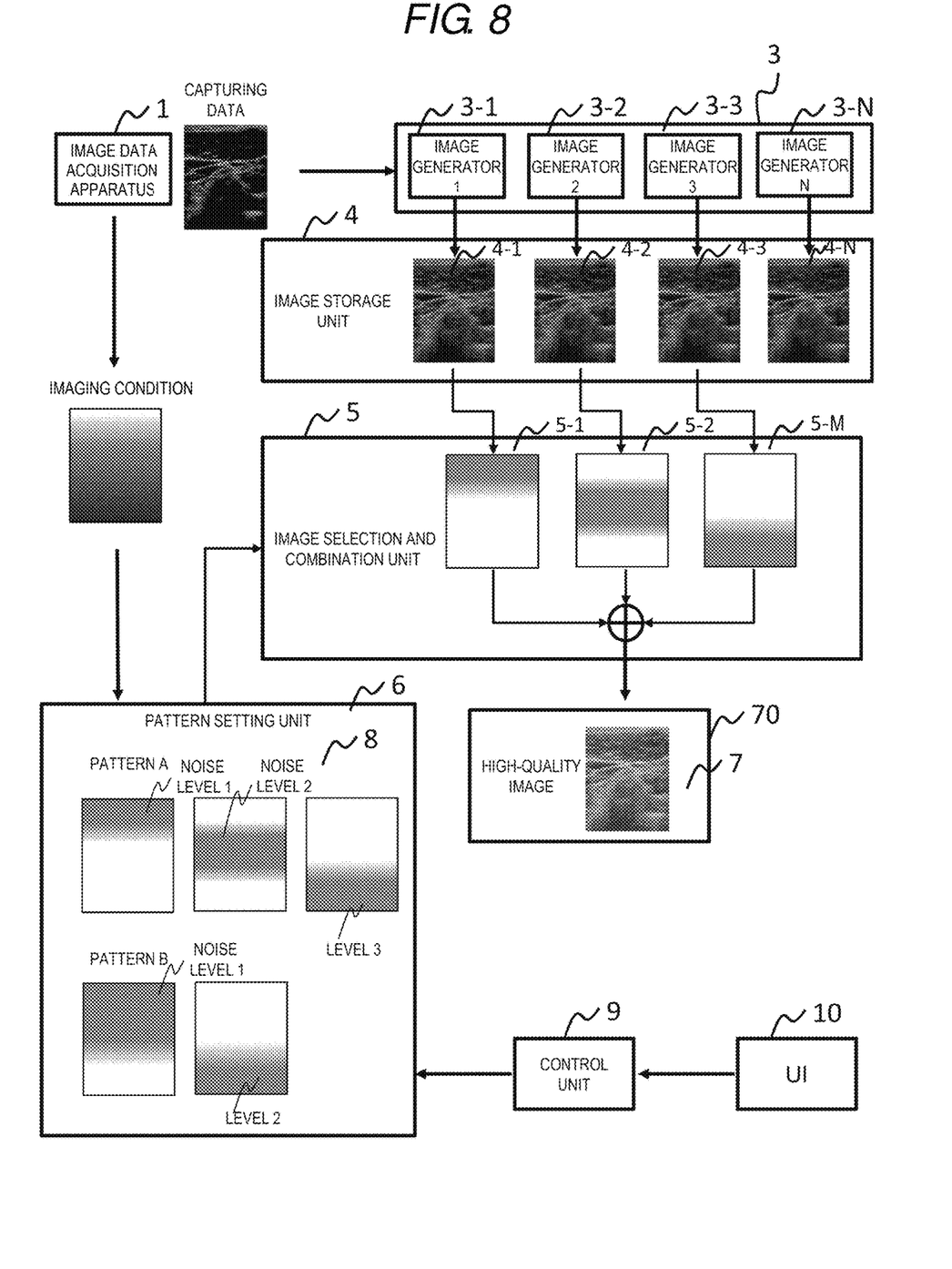
FIG. 8 is a block diagram showing the configuration of the medical imaging apparatus according to the second embodiment and a flow of processing.

As shown in FIGS. 7 and 8, the configuration of the image processing apparatus 2 is similar to that of the image processing apparatus 2 according to the first embodiment. Since a noise level of an ultrasonic image increases as a depth of a subject increases, a region selection pattern is a pattern in which a region having a shallowest noise level 1 is selected and a region which is deeper as the noise level increases is selected.

The image processing apparatus 2 according to the second embodiment includes an imaging condition reception and pattern selection unit 11. The imaging condition reception and pattern selection unit 11 receives the imaging condition from the image data acquisition apparatus 1, selects a region selection pattern suitable for the received imaging condition based on a predetermined relationship between the imaging condition and the type of the region selection pattern, and outputs the selected region selection pattern to the pattern setting unit 6. The pattern setting unit 6 sets the region selection pattern received from the imaging condition reception and pattern selection unit 11 in the image selection and combination unit 5.

Accordingly, it is possible to set the region selection pattern suitable for the imaging condition.

In addition to the predetermined relationship between the imaging condition and the type of the region selection pattern, the imaging condition reception and pattern selection unit 11 may be configured to store a relationship between the region selection pattern selected by the user and the imaging condition at that time when the user selects the region selection pattern from the receiving unit 10. Accordingly, the next time the captured image is received from the ultrasonic capturing apparatus under the same imaging conditions, the region selection pattern previously selected by the user can be selected, so that the high-quality image according to the preference of the user can be displayed.

Other configurations, operations, and effects of the image processing apparatus 2 are similar to those of the first embodiment, and thus description thereof will be omitted.

The imaging condition reception and pattern selection unit 11 in the second embodiment can also be disposed in the image processing apparatus 2 in the first embodiment.

<Overall Configuration of Ultrasonic Imaging Apparatus>

Next, an overall structure of the capturing apparatus (ultrasonic imaging apparatus) 1 according to the second embodiment will be described with reference to FIG. 9.

The ultrasonic imaging apparatus includes a transmission unit 211, a reception unit 212, an image generation unit 213, and a transmission and reception separation unit 216. The transmission unit 211 outputs a transmission signal to an ultrasonic probe 222 via the transmission and reception separation unit 216. Accordingly, the ultrasonic probe 222 transmits an ultrasonic wave 223 to a subject 220. An echo from the subject 220 is received by the ultrasonic probe 222, and the ultrasonic probe 222 outputs a reception signal. The reception unit 212 that receives the reception signal from the ultrasonic probe via the transmission and reception separation unit 216 performs reception beamforming on the reception signal along a predetermined reception scanning line. The image generation unit 213 processes the reception signal after the reception beamforming to generate an ultrasonic image. The image processing apparatus 2 receives and processes the image generated by the image generation unit 213 as the captured image.

Figure 9:
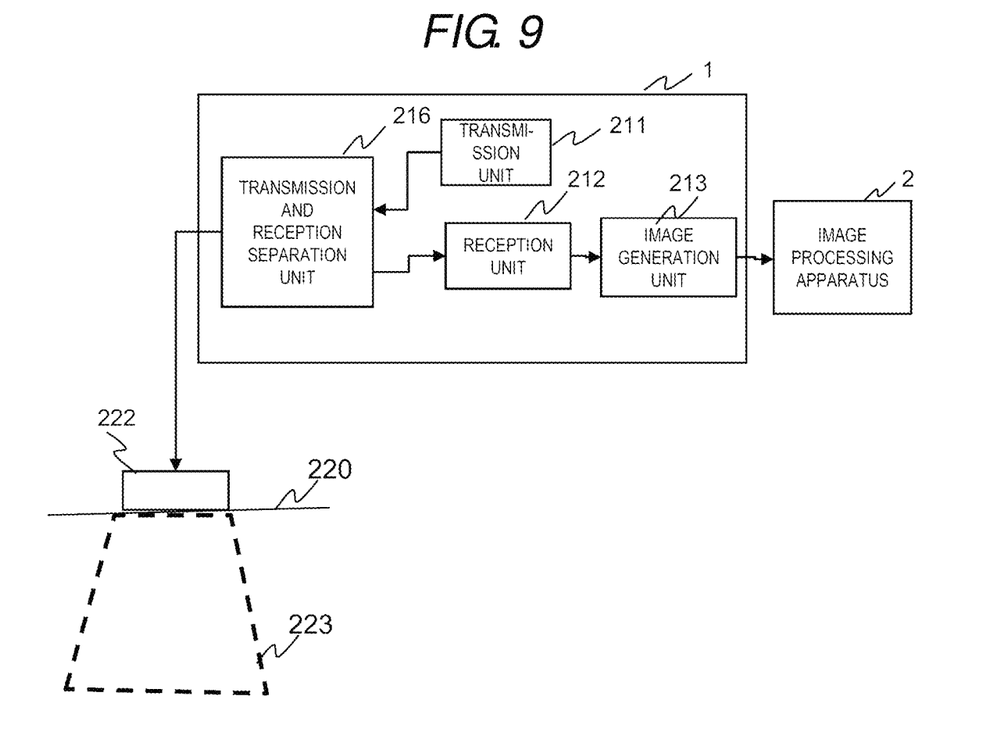
FIG. 9 is a block diagram showing a configuration of an ultrasonic capturing apparatus as a capturing apparatus of the medical imaging apparatus according to the second embodiment.

In FIG. 9, the image processing apparatus 2 is disposed after the image generation unit 213, whereas time series data before the image is generated may be input to the image generators 1 to N. Since time of the time series data corresponds to a depth of a non-subject, the noise level is divided according to a time point of the data.

What is claimed is:

1. An image processing apparatus comprising:
a processor configured to:
receive measurement data or a captured image obtained by a capturing apparatus and generate different images for a same imaging range; and
select different image regions from the generated images according to a predetermined region selection pattern, and generate one image by combining the images of the selected image regions.

2. The image processing apparatus according to claim 1, wherein the processor is further configured to:
generate an image from which noise is removed from an image having different noise levels.

3. The image processing apparatus according to claim 2, wherein
the measurement data or the captured image obtained by the capturing apparatus has different noise levels depending on a spatial region, and
the region selection pattern corresponds to a pattern of the region having different noise levels.

4. The image processing apparatus according to claim 2, wherein the processor is further configured to:
function as a plurality of trained learning models.

5. The image processing apparatus according to claim 4, wherein
each of the learning models is trained in advance using, as input data, an image in a region having a predetermined noise level among captured images having different noise levels depending on spatial regions, which are captured by the capturing apparatus by a predetermined capturing method, and using, as teacher data, a captured image captured by the capturing apparatus by a capturing method in which the noise is further reduced as compared with the capturing method.

6. The image processing apparatus according to claim 5, wherein
the capturing method for obtaining the image of the input data is a predetermined high-speed capturing method, and the capturing method for obtaining the image of the teacher data is a low-speed capturing method as compared with the high-speed capturing method.

7. The image processing apparatus according to claim 1, further comprising:
at least one storage configured to store a plurality of types of the predetermined region selection patterns used for selection; and
wherein the processor is further configured to:
select the region selection pattern from the at least one storage unit and set the selected region selection pattern, and
generate an image according to the set region selection pattern.

8. The image processing apparatus according to claim 7, wherein the at least one storage is configured to store the generated images; and wherein the processor is further configured to:
receive a selection instruction of the region selection pattern from a user.

9. The image processing apparatus according to claim 8, wherein the processor is further configured to:
after generating the one image according to the region selection pattern, receive selection of the region selection pattern from the user, set the selected region selection pattern and generate an image according to the set region selection pattern using the images stored in the at least one storage.

10. The image processing apparatus according to claim 7, wherein the processor is further configured to:
receive an imaging condition from the capturing apparatus and select a region selection pattern corresponding to the received imaging condition based on a predetermined relationship between the imaging condition and the region selection pattern, and
set the selected region selection pattern.

11. The image processing apparatus according to claim 8, wherein the processor is further configured to:
receive an imaging condition from the capturing apparatus, store the imaging condition and the region selection pattern selected by a user in association with each other, and select the stored region selection pattern the next time the imaging condition is set in the capturing apparatus, and
set the selected region selection pattern.

12. The image processing apparatus according to claim 1, wherein
the region selection pattern is set so that boundaries of regions overlap with one another by a predetermined width, and
when combining the images of the selected image regions, the processor is further configured to weight and add the image regions in the regions whose boundaries overlap with one another by the predetermined width.

13. The image processing apparatus according to claim 8, wherein the processor is further configured to:
receive a degree of change from a user, and the region selection pattern is associated with the degree of change in advance, and
set the region selection pattern associated with the degree of change in accordance with the degree of change set by a user.

14. A medical imaging apparatus comprising:
a capturing apparatus; and
the image processing apparatus according to claim 1.

15. The medical imaging apparatus according to claim 14, wherein
the capturing apparatus is a magnetic resonance imaging apparatus including a static magnetic field generation unit configured to apply a static magnetic field to a subject, a gradient magnetic field generation unit configured to apply a gradient magnetic field to the subject, a transmission coil configured to irradiate the subject with a high-frequency magnetic field, a reception coil configured to measure a nuclear magnetic resonance signal generated by the subject, and an image reconstruction unit configured to reconstruct the image based on a signal measured by the reception coil, and
the image processing apparatus is configured to receive, as the measurement data or the captured image, the signal measured by the reception coil or the image reconstructed by the image reconstruction unit.

16. The medical imaging apparatus according to claim 15, wherein the magnetic resonance imaging apparatus is configured to reconstruct the image by parallel imaging, and the region selection pattern of the image processing apparatus is configured to set the image region based on a G factor map of the parallel imaging.

17. The medical imaging apparatus according to claim 14, wherein the capturing apparatus is an ultrasonic capturing apparatus including a transmission unit configured to transmit an ultrasonic wave from an ultrasonic probe to a subject, a reception unit configured to receive a reception signal from the ultrasonic probe that receives an echo from the subject and perform reception beamforming, and an image generation unit configured to process the reception signal after the reception beamforming and generate an image, and the image processing apparatus is configured to receive the image generated by the image generation unit as the captured image.

18. The ultrasonic capturing apparatus according to claim 17, wherein the region selection pattern of the image processing apparatus is configured to set a plurality of the image regions in a depth direction of the subject.

19. A non-transitory computer readable storage medium storing an image processing program that when executed by a processor of a computer configures the processor to:

receive measurement data or a captured image obtained by a capturing apparatus and generate different images for a same imaging range; and select different image regions from the generate images according to a predetermined region selection pattern, and generate one image by combining the images of the selected image regions.

* * * * *